(12) United States Patent
Foguet et al.

(10) Patent No.: US 6,894,032 B2
(45) Date of Patent: May 17, 2005

(54) USE OF CDP-CHOLINE FOR THE TREATMENT OF ALCOHOL WITHDRAWAL SYNDROME

(75) Inventors: Rafael Foguet, Barcelona (ES); Jorge Ramentol, Barcelona (ES); Rafael Lozano, Barcelona (ES); Julián Agut, San Cugat (ES); Jesús Torres, Barcelona (ES); Manuel M. Raga, Barcelona (ES); Josep M. Castello, Barcelona (ES); José A. Ortiz, Barcelona (ES)

(73) Assignee: Ferrer Internacional, S.A., Barcelona (ES)

( * ) Notice: Subject to any disclaimer, the term of this patent is extended or adjusted under 35 U.S.C. 154(b) by 122 days.

(21) Appl. No.: 10/240,159

(22) PCT Filed: Mar. 28, 2001

(86) PCT No.: PCT/EP01/03536

§ 371 (c)(1),
(2), (4) Date: Sep. 30, 2002

(87) PCT Pub. No.: WO01/72288

PCT Pub. Date: Oct. 4, 2001

(65) Prior Publication Data

US 2003/0162749 A1 Aug. 28, 2003

(30) Foreign Application Priority Data

Mar. 29, 2000 (ES) ........................ P200000765

(51) Int. Cl.[7] ...................... A61K 31/70; A61K 31/505; A61K 31/685; A61K 31/205
(52) U.S. Cl. ............................ 514/49; 514/50; 514/78; 514/274; 514/556
(58) Field of Search ........................... 514/49, 274, 78, 514/162, 556

(56) References Cited

U.S. PATENT DOCUMENTS

| | | | |
|---|---|---|---|
| 5,958,896 A | * | 9/1999 | Renshaw et al. .............. 514/49 |
| 6,103,703 A | * | 8/2000 | Renshaw et al. .............. 514/49 |
| 2002/0019364 A1 | | 2/2002 | Renshaw |
| 2003/0220291 A1 | | 11/2003 | Renshaw |

FOREIGN PATENT DOCUMENTS

| WO | 99 07385 A | 2/1999 | |
|---|---|---|---|
| WO | WO 01/68104 A | * 9/2001 | .......... A61K/31/70 |

OTHER PUBLICATIONS

"Is Ethanol a Neurotoxin?: The Effects of Ethanol on Neuronal Structure and Function", Leonard, B.E., Alcohol Alcohol, 1986, 21(4), 325–338.*

Tornos M.E. et al., "Effect of oral CDP–choline on experimental withdrawal syndrome.", Arzneimittel–Forschung, vol. 33, 7a, pp. 1018–11021, (1983).

Renshaw P.F., et al., "Short–term treatment with citicoline (CDP–choline) attenuates some measures of craving in cocaine–dependant subjects: a preliminary report", PSYCHOPHARMACOLOGY, vol. 142, no. 2, pp. 132–138, (1999).

Patt, S. Cervos–Navarro J. et al., "The effects of CDP–choline on newborn rat pups with experimental alcohol fetopathy. A Golgi study", History and Histopathology, vol. 4, no. 4, pp. 429–434, (1989).

* cited by examiner

*Primary Examiner*—Vickie Kim
*Assistant Examiner*—Brian-Yong S. Kwon
(74) *Attorney, Agent, or Firm*—Birch, Stewart, Kolasch & Birch, LLP

(57) ABSTRACT

The invention relates to the use of CDP-Choline or its pharmaceutically acceptable salts for the preparation of a medicinal product for the treatment of alcohol withdrawal syndrome at daily doses equivalent to 0.5–2 g of free CDP-Choline.

5 Claims, No Drawings

USE OF CDP-CHOLINE FOR THE TREATMENT OF ALCOHOL WITHDRAWAL SYNDROME

This application is the national phase under 35 U.S.C. § 371 of PCT International Application No. PCT/EP01/03536 which has an International filing date of Mar. 28, 2001, which designated the United States of America.

DESCRIPTION

The present invention relates to the use of CDP-choline for the treatment of alcohol withdrawal syndrome.

The toxic effects of alcohol on central nervous system are basically exerted on neuronal membrane and synapses (Leonard B. E., *Alcohol Alcohol.*, 1986: 21(4), 325–338). Histological alterations of neuronal structure consist in a lesser branching of hippocampus nerve cells and Purkinje's cells. Comparison of brains from healthy subjects with those from alcoholic patients revealed a lesser branching of pyramidal neuronal basal dendrites in upper cerebral cortex and motor cortex (Ledig M. and Mandel P., *M S-Medecine Sciences*, 1988: 4(6), 352–357).

Chronic alcohol abuse has also been reported to impair dopamine receptor sensitivity. This effect is probably related to changes in neuronal membrane fluidity and in the number and functionality of receptors, as well as to a decrease in acetylcholine reuptake and dopamine deficiency (Carlen P. L. and col., *Ann. Neurol.*, 1981: 9(1), 84–86).

CDP-choline (cytidine diphosphate choline, Citicoline) is a key intermediate in the synthesis of structural phospholipids present in the neuronal membrane (Kennedy E. P. and Weiss S. B., *J. Biol. Chem.*, 1956; 222, 193–214) and plays an important role in its formation and repair when the phospholipidic structure is damaged by endogenous or exogenous causes involving a decrease in cytidine and choline uptake.

The administration of CDP-choline enhances dopamine synthesis and release (Martinet M. et al., *Biochem. Pharmacol.*, 1981: 30(5), 539–541) as well as choline and acetylcholine brain levels. The administration of repeated doses of CDP-choline produces an increase of brain phospholipid levels, which is secondary to an increase of cytidine and choline plasma levels (Agut J. et al., *Ann. New York Acad. Sci.*, 1993: 695, 318–320).

Surprisingly, the applicants have found out that the administration of CDP-choline to alcoholic patients reduces the duration and intensity of their withdrawal symptoms and induces an evident recovery in a significant proportion of patients.

The use of CDP-choline according to the present invention, which includes a method for treating alcohol withdrawal syndrome, comprises the administration of an effective amount of CDP-choline or a pharmaceutically acceptable salt thereof to an alcoholic patient.

According to the present invention, CDP-choline is administered as free compound or as a pharmaceutically acceptable salt, whether in anhydrous or hydrated form, conveniently mixed with pharmaceutical carriers and/or excipients, to humans at daily doses of 0.5 to 2 g inclusive in free CDP-choline, preferably from 0.5 to 1 g inclusive, both orally and parentally. Pharmaceutically acceptable salts of CDP-choline include its alkaline or alkaline earth salts, such as its sodium, potassium, calcium and magnesium salts or its acid addition salts with a mineral or organic acid, such as hydrochloric acid, hydrobromic acid, sulphuric acid, phosphoric acid, acetic acid, trifluoroacetic acid, citric acid, lactic acid, malonic acid, tartaric acid, acrylic acid, metacrylic acid, malic acid, maleic acid, fumaric acid, benzoic acid, salicylic acid, cinnamic acid, methane sulphonic acid, benzenesulphonic acid, p-toluensulphonic acid and nicotinic acid.

CDP-choline and its salts, whether as anhydrous or hydrated substances, under the invention may be administered orally in the form of tablets, capsules, powder, granules, cachets, lozenges, solution, suspension, emulsion, syrup, gel and the like; or parenterally in the form of solution, suspension, emulsion or the like for intravenous or intramuscular injection.

EXAMPLES

The present invention is illustrated by the Examples that follow. Those skilled in the art will be able to make any change provided the specific embodiment of the invention is not modified and, therefore, the invention is not limited to the specific details of the Examples.

Example 1

500 mg Tablets

| | |
|---|---|
| CDP-choline, sodium salt | 522.5 mg |
| Talc | 30.0 mg |
| Magnesium stearate | 3.0 mg |
| Silicon dioxide | 2.5 mg |
| Croscarmellose sodium | 20.0 mg |
| Corn starch | 20.0 mg |
| Microcrystalline cellulose s.q. | 780.0 mg |

Example 2

25% Oral Solution

| | |
|---|---|
| CDP-choline, sodium salt | 26.12 g |
| 70% Sorbitol | 20.00 g |
| Methyl p-hydroxybenzoate | 0.16 g |
| Propyl p-hydroxybenzoate | 0.04 g |
| Disodium citrate | 0.60 g |
| Saccharin sodium | 0.02 g |
| Strawberry essence | 0.04 g |
| Red Punzo 4R | 0.50 mg |
| Anhydrous citric acid | 0.05 g |
| Purified water s.q. | 100.00 ml |

Example 3

Solution for Injection

| | |
|---|---|
| CDP-choline, sodium salt | 522.50 mg |
| Hydrochloric acid, pH 6.0–6.5 s.q. | |
| Water for injection s.q. | 4.00 ml |

Example 4

Open Clinical Study of CDP-choline in Alcohol Withdrawal Syndrome

The progress of alcohol withdrawal syndrome was assessed in an open study conducted in 197 patients. CDP-choline was administered at doses of 500 mg/d i.m. or 600 mg/d p.o. for 60 days. At 30 and 60 days following treatment, significant differences (p<0.001) were observed in the assessments performed. At 60 days, 55.83% of patients had given up drinking alcohol and 31.97% of patients drank much less. A significant improvement was observed on anxiety, tremor, disorientation, insomnia, dysarthria, tendency to suicide and neuritic pains.

Example 5

Open, Randomized, Comparative Clinical Study of CDP-Choline in Alcohol Withdrawal Syndrome Versus Clomethiazole and Vitamin B An open, randomized and comparative study on the conventional therapy of alcohol withdrawal syndrome was conducted in 40 patients. Patients were randomly distributed in two groups of 20. One of the groups was used as control and received clomethiazole and vitamin $B_1$, $B_6$ and $B_{12}$. This treatment regimen was maintained for 8 days, and then patients were given diazepam until completion of treatment (60 days). The other group of patients received the same treatment regimen plus CDP-choline 500 mg i.m. every 12 h for the first 30 days and CDP-choline 200 mg p.o. every 8 h for the remaining 30 days. The patients who received CDP-choline plus the conventional therapy showed significant differences versus control at 30 days following treatment in tremor incidence (p<0.05), cramps (p<0.05), asthenia (p<0.05), emotional lability (p<0.01), nervousness (p<0.05) and social withdrawal (p<0.05).

What is claimed is:

1. A method for the treatment of alcohol withdrawal syndrome comprising administering to an alcoholic patient in need thereof an effective amount of CDP-choline or of a pharmaceutically acceptable salt thereof.

2. The method for the treatment of alcohol withdrawal syndrome according to claim 1, wherein the pharmaceutically acceptable salts of CDP-choline are alkaline or alkaline earth salts or salts with mineral or organic acids.

3. The method for the treatment of alcohol withdrawal syndrome according to claim 2 or 1 at daily doses in equivalent amounts of free CDP-choline ranging from 0.5 to 2 g.

4. The method for the treatment of alcohol withdrawal syndrome according to claim 3, wherein the doses range from 0.5 to 1 g.

5. The method for the treatment of alcohol withdrawal syndrome according to claim 1, wherein the pharmaceutically acceptable salts of CDP-choline are alkaline or alkaline earth salts or salts with mineral or organic acids selected from the group consisting of hydrochloric acid, hydrobromic acid, sulphuric acid, phosphoric acid, acetic acid, trifluoroacetic acid, citric acid, lactic acid, malonic acid, tartaric acid, acrylic acid, metacrylic acid, malic acid, maleic acid, fumaric acid, benzoic acid, salicylic acid, cinnamic acid, methane sulphonic acid, benzenesulphonic acid, p-toluensulphonic acid and nicotinic acid in anhydrous or hydrated form.

* * * * *